United States Patent
Samimi

(10) Patent No.: US 9,498,250 B2
(45) Date of Patent: Nov. 22, 2016

(54) APPARATUS AND METHOD FOR PERFORMING INTRASTROMALABDOMINAL HYSTERECTOMY AS BLOODLESS NERVE SPARING METHOD

(71) Applicant: Daryoosh Samimi, Fountain Valley, CA (US)

(72) Inventor: Daryoosh Samimi, Fountain Valley, CA (US)

( * ) Notice: Subject to any disclaimer, the term of this patent is extended or adjusted under 35 U.S.C. 154(b) by 311 days.

(21) Appl. No.: 14/092,250

(22) Filed: Nov. 27, 2013

(65) Prior Publication Data

US 2015/0148799 A1    May 28, 2015

(51) Int. Cl.
*A61B 18/18*    (2006.01)
*A61B 17/42*    (2006.01)
*A61B 18/00*    (2006.01)
*A61B 18/08*    (2006.01)

(52) U.S. Cl.
CPC ............ *A61B 17/42* (2013.01); *A61B 18/08* (2013.01); *A61B 2017/4216* (2013.01); *A61B 2017/4225* (2013.01); *A61B 2018/00273* (2013.01); *A61B 2018/00559* (2013.01); *A61B 2018/00601* (2013.01); *A61B 2090/08021* (2016.02)

(58) Field of Classification Search
CPC .......... A61B 18/082; A61B 2018/00559; A61B 2018/00601; A61B 2018/0237; A61B 2018/1412; A61B 18/14; A61B 17/42
See application file for complete search history.

(56) References Cited

U.S. PATENT DOCUMENTS

| | | | |
|---|---|---|---|
| 3,858,586 A * | 1/1975 | Lessen ................ | A61B 17/42 128/831 |
| 4,998,527 A * | 3/1991 | Meyer ................ | A61B 1/015 600/104 |
| 5,032,124 A * | 7/1991 | Menton ................ | A61B 18/24 606/14 |
| 5,662,676 A * | 9/1997 | Koninckx .......... | A61B 17/0218 600/210 |
| 6,254,601 B1 * | 7/2001 | Burbank ............... | A61B 8/06 128/898 |
| 6,572,631 B1 * | 6/2003 | McCartney ............. | A61B 1/32 606/119 |
| 2010/0082038 A1 * | 4/2010 | Samimi ................. | A61B 17/42 606/119 |
| 2010/0280524 A1 * | 11/2010 | Lopez Zepeda ... | A61B 17/4241 606/119 |

* cited by examiner

*Primary Examiner* — Joseph Stoklosa
*Assistant Examiner* — Amanda Zink
(74) *Attorney, Agent, or Firm* — Plager Schack LLP

(57) ABSTRACT

An apparatus and procedure for defining the area for a thermo-electric knife to perform a bloodless intrastromal abdominal hysterectomy procedure while minimizing damage to the pericervical ring. The apparatus is configured to be inserted into the center cavity of the cervix and uterus to engage the uterine wall. The apparatus comprises an elongate member having a first end configured to extend into the center cavity of the uterus and cervix, and a thermo-electric knife guide plate secured concentrically to the elongate member proximal to the second end of the member to define the area for dissection of connective tissue between the cervix and the pericervical ring by a thermo-electric knife. A barb is secured to the elongate member between the first end and the guide plate, and configured to engage the uterine wall so that upon removal of the apparatus when in use the barb becomes attached to the uterus sufficient to remove the uterus and cervix through the abdomen. At least one aperture in the guide plate is configured to permit the passage therethrough of a centering tube when in use, whereby the apparatus is configured to stabilize the thermo-electric knife during intrastromal abdominal hysterectomy procedure.

8 Claims, 4 Drawing Sheets

APPARATUS AND METHOD FOR PERFORMING INTRASTROMAL ABDOMINAL HYSTERECTOMY AS BLOODLESS NERVE SPARING METHOD

BACKGROUND

The embodiments herein relate generally to an apparatus and method for performing intrastromal abdominal hysterectomy as a bloodless nerve-sparing method without disrupting or otherwise damaging the pelvic support. More specifically, the invention relates to a device and method for performing an intrastromal abdominal hysterectomy that generally minimizes damage to the pericervical ring, reduces the risk of cervical cancer, reduces hospital stay, and reduces post-operation complications, such as post-operation infections, ureter injuries, vaginal vault prolapse and post-hysterectomy fistula.

Cervical cancer is said to be the second most common cancer found worldwide among women, the third most common cause of cancer-related deaths, and the most common cause of mortality from a gynecologic malignancy. Some of the causes of cervical cancer can be attributed to other types of medical surgical procedures performed within the female reproduction anatomy.

For instance, one of the relatively common procedures performed today is a supracervical hysterectomy. A supracervical hysterectomy is one alternative of a hysterectomy that may be performed to treat medical conditions such as benign fibroid tumors of the uterus, ovarian cysts, endometriosis, abnormal uterine bleeding and chronic pelvic pain without affecting urinary continence or sexual function. As a result, in a supracervical hysterectomy, the uterus is removed but leaves the cervix in place.

The resulting disadvantage of a supracervical hysterectomy is that often a treating physician will find that a patient who had this procedure done in the past has now developed a cervical disease in the cervical stump. Some of the problems that arise from the residual cervical stump are pain, bleeding, necrosis, recurrence of fibroids, and the development of cancer. In fact, the supracervical hysterectomy procedure has been criticized in medical literature due to the potentially fatal cancer that can develop in the cervical stump.

Another disadvantage associated with the supracervical hysterectomy is that it is expensive due to the cancer preventative measures that are taken into account. For example, there are varying preventive measures a doctor may recommend or prescribe to a patient who has undergone a supracervical hysterectomy that has left a cervical stump.

When a doctor determines that the removal of the patient's cervix is the best option, the patient will have to undergo a hysterectomy in order to remove the cervix. One method of performing a hysterectomy is an abdominal hysterectomy. This is considered within the medical community as a conventional method of performing a hysterectomy.

In the conventional abdominal hysterectomy, a surgeon may remove the cervix by cutting the uterosacral ligaments, the cardinal ligament of Mackenrodt, and the uterine vessel, all before entering the vaginal fornix. Once the ligaments are cut, the cervix is then severed from the vagina in a circular manner at the cervico-vaginal junction. Typically, in order to access the cervico-vaginal junction, the bladder is pushed downwards, or is even dissected free of its attachments.

As a result of this conventional hysterectomy, significant damage occurs to the Franken Hauser's nerve plexus, the vesical plexus, and other downstream nerves. Also a problematic result is that fibrous condensation in the endopelvic fascia is severed and is no longer able to support the vaginal vault.

Furthermore, in the conventional hysterectomy, substantial blood loss may occur as well as other post-operative complications, such as infections, ureter injuries, vaginal vault prolapses and post-hysterectomy fistula.

There is a need in the art for a device and procedure to perform a hysterectomy without severing the surrounding nerves and without disturbing the pelvic support system. Specifically, there is a need for a device and method that provides a means to make a precise incision in the cervical area to remove the cervix without severing or adversely affecting any of the surrounding nerve structures of the pericervical ring, reproductive organs, or other surrounding anatomical systems. There is also a need for an apparatus and method to perform a hysterectomy that does not result in post-operation infections, ureter injuries, vaginal vault prolapses and posthysterectomy fistula. There is also a need for an apparatus and method for performing a hysterectomy that does not result in significant blood loss or the necessity of a transfusion. There is also a need for an apparatus and method for performing a hysterectomy that does not result in a prolonged hospital stay. There is also a need for an apparatus and method for performing a hysterectomy that can prevent or reduce the likelihood of the occurrence of cervical cancer.

It is an objective of the present invention to facilitate and perform an intrastromal abdominal hysterectomy with the claimed device as a bloodless nervesparing method without disturbing the pelvic support system.

It is another objective of the present invention to perform an intrastromal abdominal hysterectomy with the claimed device as an alternative procedure to prevent blood loss and the need for transfusions.

It is another objective of the present invention to perform an intrastromal abdominal hysterectomy with the claimed device to enable a shorter hospital stay.

It is another objective of the present invention to perform an intrastromal abdominal hysterectomy with the claimed device in order to prevent post-operative conditions, such as post-operation infections, ureter injuries, vaginal vault prolapses and post-hysterectomy fistula.

It is another objective of the present invention to perform an intrastromal abdominal hysterectomy with the claimed device in order to prevent cervical cancer.

It is another objective of the present invention to perform an intrastromal abdominal hysterectomy with the claimed device that maintains the cardinal and uterosacral ligaments, nerve fibers, and pericervical ring as un-severed and intact.

Finally, it is yet another objective of the present invention to provide a way to perform an intrastromal abdominal hysterectomy with a device, as claimed, that helps to identify the anatomy during the surgical procedure.

These and other objectives, advantages and features of the present invention are described herein with specificity so as to make the present invention understandable to one of ordinary skill in the art.

SUMMARY

The claimed apparatus defines an area for a thermoelectric knife to perform a bloodless intrastromal abdominal hysterectomy procedure while minimizing damage to the pericervical ring, the apparatus configured to be inserted into the center cavity of the cervix and uterus to engage the uterine wall. The apparatus comprises an elongate member having a first end and second end, the first end configured to extend into the center cavity of the uterus and cervix. A thermo-electric knife guide plate is secured concentrically to the elongate member proximal to the second end of the member to define the area for dissection of connective tissue between the cervix and the pericervical ring by a thermo-electric knife. A barb is secured to the elongate member between the first end and the guide plate. The barb configured to engage the uterine wall so that upon removal of the apparatus when in use the barb becomes attached to the uterus sufficient to remove the uterus and cervix through the vagina. There is at least one aperture in the guide plate configured to permit the passage therethrough of a centering tube when in use, whereby the apparatus is configured to stabilize the thermo-electric knife during intrastromal abdominal hysterectomy procedure.

The claimed procedure for performing a bloodless intrastromal abdominal hysterectomy which minimizes damage to the pericervical ring during dissection of connective tissue between the cervix and the pericervical ring comprises the first step of inserting, vaginally, an apparatus into the center cavity of the uterus and cervix. The apparatus is configured to define the area for dissection of connective tissue between the cervix and the pericervical ring by a thermo-electric knife, and to engage the uterine wall so that upon removal of the apparatus the uterus and cervix are also removed through the abdomen. Second, the apparatus is stabilized by the inserting a tube through an aperture in the knife guide plate which is secured concentrically to the elongate member of the apparatus to engage the uterine wall. Third, the connective tissue of the uterus is dissected from the pericervical ring using a thermo-electric knife in conjunction with the guide plate of the apparatus to guide a thermo-electric knife around the inner diameter of the pericervical ring to gradually dissect the connective tissue between the cervix and the pericervical ring. Last, the apparatus which engages the cervix and uterus are removed by pulling the apparatus and cervix connected to the uterus out through the abdomen.

BRIEF DESCRIPTION OF THE FIGURES

The detailed description of some embodiments of the invention will be is made below with reference to the accompanying figures, wherein like numerals represent corresponding parts of the figures. Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

DETAILED DESCRIPTION OF CERTAIN EMBODIMENTS

In the following discussion that addresses a number of embodiments and applications of the present invention, reference is made to the accompanying drawings that form a part hereof, where depictions are made, by way of illustration, of specific embodiments in which the invention may be practiced. It is to be understood that other embodiments may be utilized and changes may be made without departing from the scope of the present invention.

Before beginning a discussion of the diagrams included herein, it is asserted that the claimed device was tested in a group of twenty patients, all of whom had an intrastromal abdominal hysterectomy performed. Each of the twenty patients was operated on by the same doctor at the same institution. The length of the intrastromal abdominal hysterectomy was measured from the point at which the claimed device was applied to a patient. For each of the patients, the following parameters were evaluated: (1) pre-operative and post-operative hemoglobin levels, (2) number of days for hospital stay, (3) debility morbidity, (4) wound healing, and (5) readmission to the hospital due to ureter injury, vaginal prolapse, or posthysterectomy fistula.

In general, there were differences in the average blood loss and average hospital stay. Overall, the intrastromal abdominal hysterectomy proved to show reduced blood loss as well as shorter hospital stays. In addition, no post-operation infections, ureter injuries, vaginal vault prolapses, or post-hysterectomy fistula were seen to have resulted in any of the patients operated upon. Due to the reduced blood loss in the patients, no transfusions were needed for any of the patients. Based on this group of patients, the use of the claimed device in the intrastromal abdominal hysterectomy appears to be an effective alternative for the traditional hysterectomy that is currently performed in patients.

Figure 1:
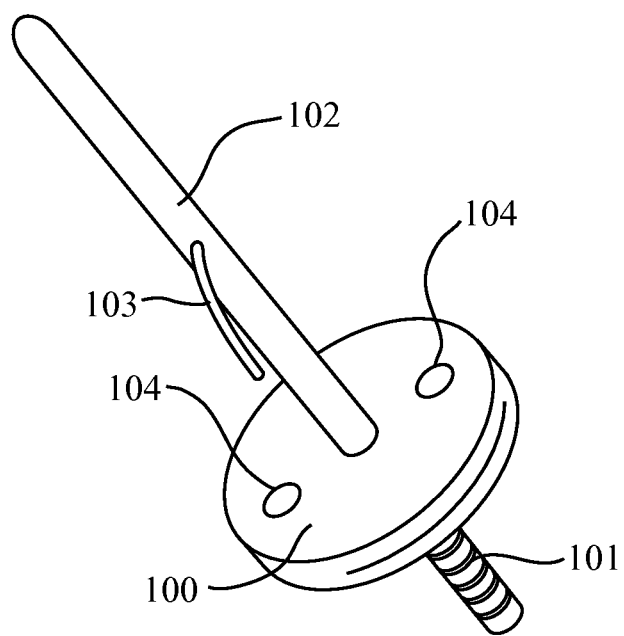
FIG. 1 is a side perspective view of the claimed apparatus that is used for performing an intrastromal abdominal hysterectomy in an exemplary embodiment of the invention. In this view, the side of the cutting guide connected to the elongated member is herein depicted. On the opposite side of the cutting guide is attached a deployment handle for use in insertion of the apparatus during the hysterectomy. At the end of the elongated member is positioned a stabilizer for use in anchoring the entire apparatus within the cervix in order to maintain its position during the hysterectomy.

Turning to FIG. 1 illustrates a side perspective view of the claimed apparatus that is used for performing an intrastromal abdominal hysterectomy. The apparatus defines the area for a thermo-electric knife or laser knife to perform an intrastromal abdominal hysterectomy procedure while minimizing damage to the pericervical ring. The apparatus is configured to be inserted into the center cavity of the uterus and to engage the uterine wall. The apparatus comprises an elongate member having a first end 102 and second end 101. The first end 102 is configured to extend into the center cavity of the uterus. A thermo-electric knife guide plate 100 secured concentrically to the elongate member proximal to the second end 101. A barb 103 is secured to the elongate member between the first end 102 and the guide plate 100.

The barb configured to engage the uterine wall so that upon removal of the apparatus when in use the barb becomes attached to the uterus sufficient to remove the uterus through the cervix. At least one aperture 104 is located in the guide plate 100. Aperture 104 is configured to permit the passage therethrough of a centering tube to stabilize the apparatus, and the thermo-electric knife during intrastromal abdominal hysterectomy procedure.

The second end is configured as a deployment handle 101. The deployment handle can be used for inserting the apparatus into a cervix and the center cavity of the uterus during an intrastromal abdominal hysterectomy. The deployment handle 101 assists in being able to properly guide the device into the cervix. The deployment handle 101 may be square or rectangular in shape with a series of parallel-positioned square-shaped concentric grooves engraved therein. The square-shaped grooves may be engraved within the deployment handle 101 for purposes of attaining a better grip whether used manually or in conjunction with a medical instrument or machine, such as a clamp.

The deployment handle 101 may vary in size, and may have the following measurements of an approximate length of 1.2 centimeters (cm) and an approximate width of 0.6 cm. While instrumental in placement of the device, the deployment handle 101 is not an essential feature of the device. In fact, other comparable ways of guiding and/or handling the device into the cervix may be used and incorporated into the device without limiting the scope of the invention.

The guide plate 100 is disc-shaped, having a substantially circular shape, and is coupled with said deployment handle 101. The exact measurements of the cutting guide 100 may vary in size; however, the cutting guide 100 may be approximately 0.3 cm in thickness and approximately 2 cm in diameter. Other shapes, such as an elliptical shape, may be employed for the cutting guide 100.

The measurements specified herein are not intended to limit the scope of the invention. It may be necessary to vary the size of the cutting guide as well as other of the device's components as appropriate. This is because a female's reproductive anatomy may differ slightly in size or shape. Typically, a cervix, or the mouth of the uterus, may range in size from 2.5 cm to 3 cm. However, a woman might have an unusually small or large cervix. For a reproductive-aged woman, her cervical canal will typically have a certain range of measurements. In addition, in a parous woman, the cervix is usually bulkier and the cervix's external os may appear wider. Thus, it may be necessary from a medical standpoint to adjust the claimed device's shape and dimension as needed for certain patients.

As explained above, the first end 102 is coupled to the opposite side of the cutting guide 100 that is coupled to the deployment handle 101. The length of the first end 102 may be approximately 4.2 cm. Thus, the entire length of the device from the end of the tip of the first end 102 to the end of the deployment handle may be approximately 5.7 cm. Overall, the first end 102 has a generally cylindrical shape. The proximal end of the first end 102 coupled to the cutting guide 100 has a substantially cylindrical shape with an approximate inner diameter of 0.6 cm. As one follows the length of the first end 102 from the end proximal to the cutting guide towards its distal end, it becomes tapered in shape, forming a tip.

At this distal end, the first end 102 may have an inner diameter of approximately 0.3 cm. The tip-shape at the distal end of the first end 102 is also a spherical radius-like shape. All parts of the claimed device, with the exception of the guide plate 103, may be made of plastic, in accordance with an exemplary embodiment of the invention.

Figure 4:
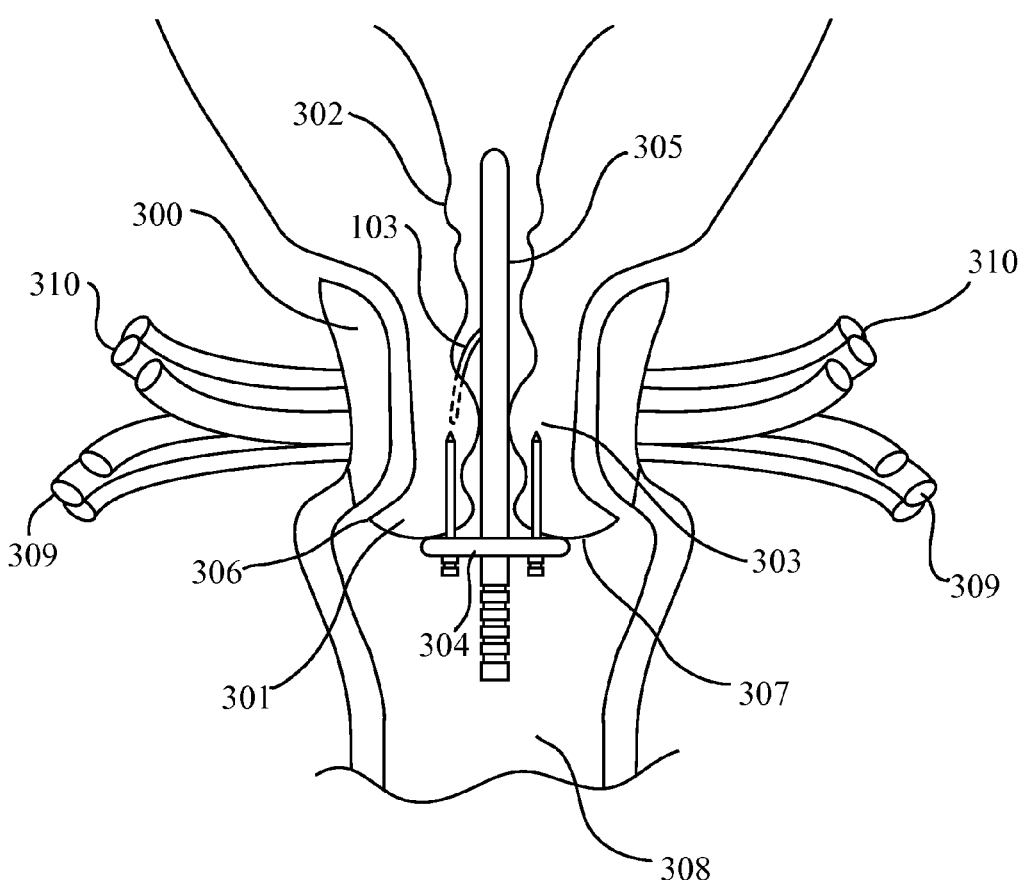
FIG. 4 illustrates a front view of the a front view of the female reproductive anatomy showing where the claimed device is inserted as used in the intrastromal abdominal hysterectomy, and further secured with two microcathethers inserted through the apertures of the plate of the apparatus.

Incorporated into the guide plate 100 is one or more apertures 104 for the deployment of a stabilizing tube. The stabilizing tube is deployed through aperture and attached to the uterine wall to stabilize the apparatus to prevent movement of the apparatus during the procedure to dissect the connective tissue between the uterus and the pericervical ring thereby freeing the uterus from the pericervical ring for removal and protecting the pericervical ring against an inadvertent damage during the dissection of the connective tissue as depicted in FIG. 4. It is preferred that two apertures are incorporated in the cutting guide plate approximately opposite each other to maximize stabilization of the apparatus with the threading of a micro-catheter through each aperture.

Although it is not an absolute requirement of the claimed device, acetal plastic is a suitable material for making the claimed device due its properties, which are usually characterized by a good fatigue life, low moisture sensitivity, high resistance to solvents and chemicals, and good electric properties. It should be noted that other comparable materials may be used to make the claimed device without deviating from the scope of the claimed invention.

The barb 103 serves the purpose of providing an anchoring or a locking function for the claimed apparatus once it is inserted into the cervix to maintain its position during the hysterectomy procedure, and to facilitate removal of the uterus at the conclusion of the procedure. In an exemplary embodiment, the barb 103 is positioned between the tip of the first end 102 and guide plate 100. The barb 103 may be approximately 1 millimeter (mm) in diameter and approximately 1 cm in length. The barb is positioned so that it is obliquely situated on the first end 102, which can be at an approximate 30 degree angle. The end of the barb 103 that is slanted upwards in the 30 degree angle generally faces in the direction of the guide plate 100.

The barb 103 may be positioned at varying angles, such as 10 degrees or 15 degrees. However, if the barb 103 is positioned at an angle of more than 30 degrees, there exists the potential for a laceration in the cervix tissue to occur when the claimed device is in use.

The barb 103 is made of a slightly flexible steel material and is integrated into the claimed device when it is formed using any convention injection molding and curing technique. It is not required that the barb 103 be coated with plastic since when used in a 30 degree angle, no damage occurs to the tissue of the cervical canal when the stabilizer is anchored therein.

The flexible steel material of the barb 103 may serve as a radio opaque marker for purposes of locating the barb 103 should it become lost or detached from the claimed device. The first end 102 may also contain a plurality of barbs in accordance with any medical concerns or other factors the doctor or surgeon may take into account with respect to anchoring the device in the cervix.

Figure 2:
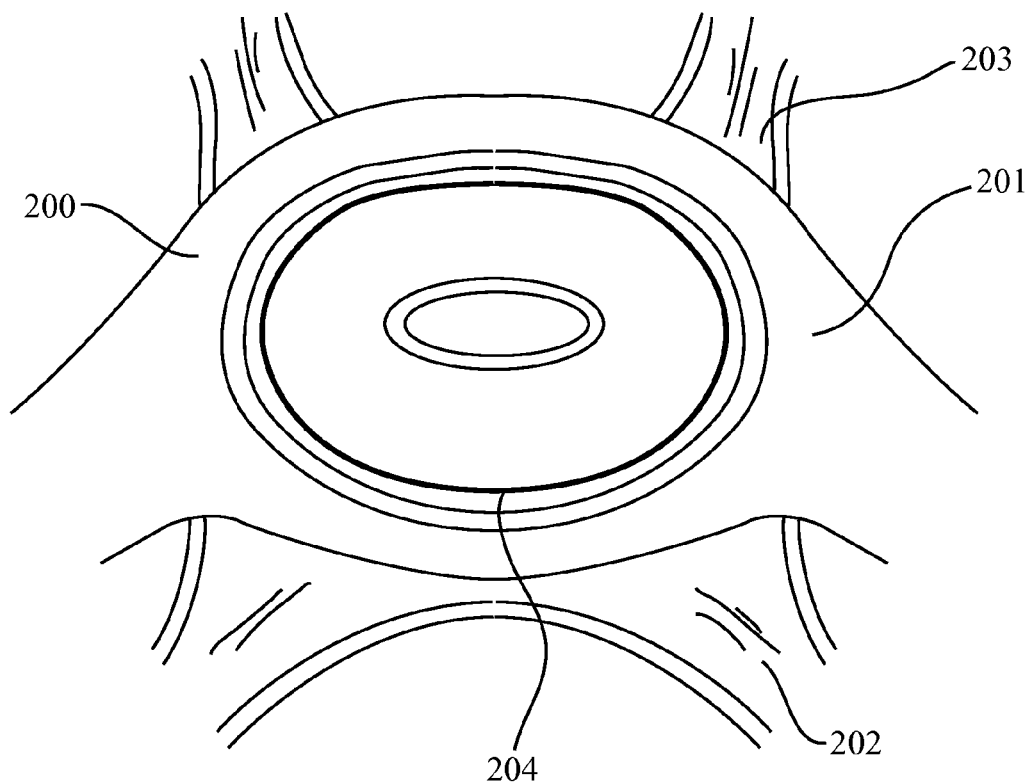
FIG. 2 illustrates a cross-sectional view of a pericervical ring of a cervix near a cervico-uterine junction where the claimed device is inserted vaginally into the cervical canal. The cutting guide is positioned proximate the center of the pericervical ring to act as guide when making an incision within the cervical stroma for purposes of ultimately removing the cervix.

FIG. 2 illustrates in a cross-sectional view at the cervico-uterine junction where the main anatomical feature, the pericervical ring 200 of the cervix, is located. It is at the pericervical ring 200 where the claimed device is used to begin the actual removal of the cervix. Even though the pericervical ring 200 is an anatomical location involved in the use of the claimed device, it is left intact and is not incised or otherwise separated or detached from the cervix or its surrounding support structures.

In fact, the claimed device assists in protecting the pericervical ring 200 during the intrastromal abdominal hysterectomy so that the surrounding nerve structures and pelvic support system are not significantly disturbed. As previously discussed, the cardinal ligament 201 and the uterosacral ligament 202 are the main support structures of the cervix. Also depicted in FIG. 2 is the vesico-cervical ligament 203, which is also attached to the peripheral portion of the cervix. When a pericervical incision 204 is made within the pericervical stroma (not shown), the surrounding ligaments 201, 202 and 203 remain substantially intact and undisturbed through the hysterectomy. The peripheral portion of the cervix should be protected since it is fused with this ligamentous support system and other nerves. Use of the claimed device protects the integrity of these ligaments to avoid the adverse results like those seen in the traditional abdominal hysterectomy.

Figure 3:
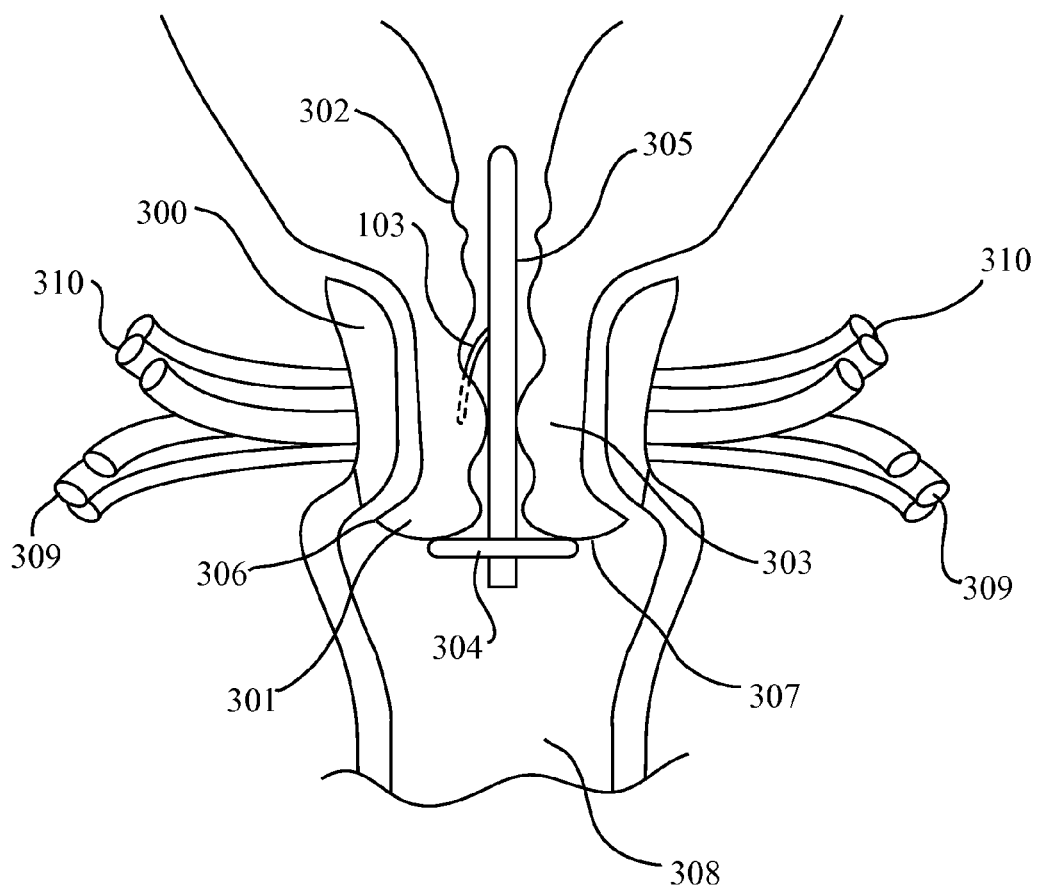
FIG. 3 illustrates a front view of the female reproductive anatomy showing where the claimed device is inserted as used in the intrastromal abdominal hysterectomy. In order to prevent against severing or otherwise adversely affecting the surrounding nerves or supporting ligaments, the claimed device, when used during the intrastromal abdominal hysterectomy, is able to assist in identifying the anatomy.

FIG. 3 illustrates a front view of the female reproductive anatomy showing where the claimed apparatus is inserted as used in the intrastromal abdominal hysterectomy. To minimize severing or otherwise adversely affecting the surrounding nerves or supporting ligaments, the claimed apparatus, when used during the intrastromal abdominal hysterectomy, is able to assist in identifying the anatomy.

Before commencing use of the claimed device, an adequate amount of vasoconstrictive solution is injected into the peripheral cervix 300 until ischemia is attained. Then the claimed device is inserted vaginally through the cervical canal 301 beginning with the portion of the claimed device containing the stabilizer 302 toward the internal os of the cervix 303 until the cutting guide 304 can no longer be pushed inwards.

In this diagram, only one barb 103 is depicted. However, as previously discussed in FIG. 1, a plurality of barbs may be integrated into the first end 102. The plurality of barbs may be placed in various positions along the length of the first end 102.

The guide plate 100 acts as guide when making an incision in the cervical canal 301 and cervical stroma 306 for purposes of ultimately removing the cervix 303. Once the guide plate 100 is in place, a thermoelectric or thermoelectric knife is used to begin making the surgical incisions from the abdominal side or above. The dissection into the cervix 303 should be performed in a substantially circular manner. Once one whole circular incision is made around the upper side of the cervical stroma 306, the claimed device is adjusted, to continue making a series of continuous circular incisions. Each incision in the series of circular incisions is made in a gradual manner and in intervals of approximately 0.5 cm at a time. By gradually performing the circular incisions in small intervals, bleeding is reduced.

The incisions should not be made in the fascia of the anterior, posterior or lateral sides of the cervix 303, rather the incisions should be made within the cervical stroma 306. The gradual incisions made within the cervical stroma 306 allow for the cervix 303 to ultimately be removed from within the pericervical ring 307. As mentioned, the claimed apparatus acts as an identifier of the anatomy throughout the process of making each incision in the cervix 303. Incisions are made until the vagina 308 is reached. Once all of the necessary incisions are made, the entire cervix 303 is removed from within the pericervical ring 307 without disturbing the surrounding support ligaments or nerves.

In FIG. 3, one can see the surrounding ligaments, specifically the cardinal ligament 309 and the uterosacral ligament 310, which are attached to the peripheral portion of the cervix 303. When the cervix 303 is removed with the claimed device, the cardinal ligament 309 and the uterosacral ligament 310 still remain substantially intact and undisturbed so as not to result in some of the adverse effects that can occur in the traditional hysterectomy.

Once the cervix 303 is removed, the surgeon is to begin making the necessary surgical closures. In order to close the pericervical ring 307, a continuous interlocking method with delay absorbable sutures are to be made starting from the vaginal margin. It should be noted that the closure of the vaginal fornix can be accomplished by using the same method of making such sutures. The remaining closures should be continued from the vaginal side toward cephalic by use of a spiral or tornado technique.

Once the upper margin of the pericervical ring 301 is closed, the surgical end of the round ligaments are to be anchored to the middle portion of the pericervical ring. By anchoring the surgical end of the round ligament, this provides for additional pelvic support. Any remaining raw surfaces should be carefully peritonealized during closure of the abdominal area.

An apparatus and method for performing an intrastromal abdominal hysterectomy has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching. It is intended that the scope of the invention not be limited by this detailed description, but by the claims and the equivalents to the claims.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method of performing a bloodless intrastromal abdominal hysterectomy procedure which minimizes damage to the pericervical ring during dissection of connective tissue between the cervix and the pericervical ring, the method comprising:

inserting, vaginally, an apparatus defining the area for dissection of connective tissue between the cervix and the pericervical ring by a thermo-electric knife into the center cavity of the uterus and cervix comprising an elongated member with a first end and second end, the first end configured to engage the center cavity of the uterus, a thermo-electric knife guide plate extending radially from said elongated member proximal to said second end, a barb configured to engage the uterine wall located between the first end of the elongated member and the plate; and at least one aperture located in the cutting guide plate through which a tube is passed to stabilize the apparatus by restricting movement of the apparatus during the procedure thereby minimizing damage to the pericervical ring during operation of the thermo-electric knife to dissect the connective tissue between the uterus and the pericervial ring toward the internal os of the cervix until the guide plate can no longer be inserted inwards;

stabilizing the apparatus by the inserting a tube through the aperture to engage the uterine wall;

dissecting the connective tissue of the uterus from the pericervical ring using a thermo-electric knife in conjunction with the guide plate of the apparatus to guide a thermo-electric knife around the inner diameter of the pericervical ring to gradually dissecting the connective tissue between the cervix and the pericervical ring;

removing the cervix and uterus engaged with the barb by pulling the apparatus and cervix connected to the uterus out through the abdomen.

2. The method of claim 1, further comprising the injecting of an adequate amount of vasoconstrictive solution into the peripheral cervix until ischemia is obtained prior to inserting the apparatus.

3. The method of claim 1 wherein the second end of the apparatus is generally square to facilitate engagement by forceps or clamps to facilitate removal of the apparatus and the uterus upon completion of the intrastromal abdominal hysterectomy procedure.

4. The method of claim 1 wherein the second end of the apparatus is generally square with at a single concentric ridge to facilitate engagement by forceps or clamps to facilitate removal of the apparatus and the uterus upon completion of the intrastromal abdominal hysterectomy procedure.

5. The method of claim 1, further comprising the step of inserting said elongated member and stabilizer into a cervical canal of said cervix from a vaginal region below said cervix toward an internal os region of said cervix.

6. The method of claim 1, further comprising the step of anchoring said cutting guide to maintain its position on said pericervical ring by attaching said barb on a middle portion of said cervical canal region of said cervix.

7. The method of claim 1, further comprising the steps of:
making a plurality of substantially circular incisions around said cutting guide within said cervical canal until said vaginal region is reached; and
reducing blood loss by separately performing each said substantially circular incision in intervals of 0.5 cm.

8. The method of claim 1, further comprising the step of removing said cervix after making said plurality of substantially circular incisions within said cervical canal without having severed any of the surrounding nerves or pelvic support system of said pericervical ring.

* * * * *